US009242121B2

(12) United States Patent
Wang et al.

(10) Patent No.: US 9,242,121 B2
(45) Date of Patent: Jan. 26, 2016

(54) ULTRASONIC TRANSDUCER

(75) Inventors: Zhibiao Wang, Chongqing (CN); Hua Wang, Chongqing (CN); Deping Zeng, Chongqing (CN); Chunliang Zhao, Chongqing (CN); Fangwei Ye, Chongqing (CN); Sanyong Li, Chongqing (CN); Guihua Xu, Chongqing (CN); Xiaobo Gong, Chongqing (CN)

(73) Assignee: CHONGQING HAIFU MEDICAL TECHNOLOGY CO., LTD., Chongqing (CN)

( * ) Notice: Subject to any disclaimer, the term of this patent is extended or adjusted under 35 U.S.C. 154(b) by 526 days.

(21) Appl. No.: 13/520,699

(22) PCT Filed: Apr. 2, 2011

(86) PCT No.: PCT/CN2011/000575
§ 371 (c)(1),
(2), (4) Date: Jul. 5, 2012

(87) PCT Pub. No.: WO2011/120340
PCT Pub. Date: Oct. 6, 2011

(65) Prior Publication Data
US 2013/0023801 A1    Jan. 24, 2013

(30) Foreign Application Priority Data

Apr. 2, 2010 (CN) .......................... 2010 1 0140052

(51) Int. Cl.
A61N 7/00 (2006.01)
A61N 7/02 (2006.01)
G10K 11/32 (2006.01)
B06B 1/06 (2006.01)
A61B 8/00 (2006.01)

(52) U.S. Cl.
CPC ................ *A61N 7/02* (2013.01); *B06B 1/0637* (2013.01); *G10K 11/32* (2013.01); *A61B 8/4455* (2013.01); *A61N 2007/006* (2013.01); *A61N 2007/0069* (2013.01); *A61N 2007/0078* (2013.01)

(58) Field of Classification Search
USPC ................................ 600/437, 407; 601/1–3
See application file for complete search history.

(56) References Cited

U.S. PATENT DOCUMENTS

| 6,419,648 | B1* | 7/2002 | Vitek et al. ......................... 601/3 |
| 2006/0058678 | A1 | 3/2006 | Vitek et al. |
| 2006/0244340 | A1* | 11/2006 | Marathe et al. ................ 310/321 |
| 2009/0230822 | A1* | 9/2009 | Kushculey et al. ........... 310/366 |
| 2009/0259129 | A1 | 10/2009 | Wang et al. |

FOREIGN PATENT DOCUMENTS

| CN | 1546219 A | 11/2004 |
| CN | 101140354 A | 3/2008 |
| WO | 2009048969 A1 | 4/2009 |

OTHER PUBLICATIONS

International Search Report dated Jul. 14, 2011 for PCT/CN11/00575.

* cited by examiner

*Primary Examiner* — Joel F Brutus
(74) *Attorney, Agent, or Firm* — Nath, Goldberg & Meyer; Joshua B. Goldberg; Christopher Thomas

(57) ABSTRACT

An ultrasonic transducer is disclosed, which includes one or a plurality of ultrasonic emitting units. Wavefronts of the ultrasonic waves emitted by the one or the plurality of ultrasonic emitting units are sphere surfaces with uniform radius, and the one or the plurality of ultrasonic emitting units can reflect ultrasound. The one ultrasonic emitting unit is configured to form a spherical resonant cavity, or the plurality of ultrasonic emitting units are configured to form a spherical resonant cavity collectively. An internal cavity of the spherical resonant cavity has a spherical shell shape or a cross-sectional spherical shell shape with a spherical center therein. The ultrasonic waves emitted by the one or the plurality of ultrasonic emitting units are focused on an area in which the spherical center of the spherical resonant cavity is located. The ultrasonic transducer not only can be provided with a large ultrasonic emitting area and a great focusing gain that render the energy of the ultrasonic focus enhanced dramatically, but also can be free from the influence of work frequency of an ultrasonic source.

20 Claims, 6 Drawing Sheets

ULTRASONIC TRANSDUCER

CROSS-REFERENCE TO RELATED APPLICATIONS

This application is a U.S. national stage application under 35 U.S.C. 371 of co-pending International Application No. PCT/CN11/00575 filed Apr. 2, 2011 and entitled ULTRASONIC TRANSDUCER which in turn claims priority to Chinese Patent Application No. 201010140052.0 filed Apr. 2, 2010, both of which are incorporated by reference herein in their entirety for all purposes.

TECHNICAL FIELD OF THE INVENTION

The present invention belongs to the field of ultrasonic therapy technology, and particularly relates to an ultrasonic transducer.

BACKGROUND OF THE INVENTION

When ultrasound is used to treat diseases, owing to the great loss of ultrasonic energy on the transmission path, the ultrasonic intensity focused at a nidus is too low to achieve required clinical therapeutic effect. Therefore, for an ultrasonic treatment apparatus, the tough technical difficulties required to be solved currently are how to reduce severe attenuation of ultrasound on transmission paths as much as possible and how to enhance ultrasonic intensity at treated parts.

In the prior art, a manner for solving the above technical problem is usually obtained by the design of an ultrasonic transducer. For an existing ultrasonic transducer, the size and intensity of the ultrasonic energy focusing area are usually relevant to the emitting area and work frequency of the ultrasonic transducer. The larger the emitting area is, the more the ultrasonic energy focused on the area is; and the higher the work frequency of the ultrasonic transducer is, the shorter the wavelength of the emitted ultrasonic waves is, thus reducing the focusing area and increasing the ultrasonic intensity.

In order to increase the emitting area of the ultrasonic transducer, an ultrasonic transducer is disclosed in US2006/0058678A1, in which ultrasonic sources are fixed on an annular supporting body to increase the emitting area of ultrasonic waves. In order to avoid mutual influence of the ultrasonic sources, the following technical solution is adopted in the design: the ring surface opposite to each ultrasonic source is configured as a notch, therefore, the ultrasonic transducer obtains enhanced focusing gain relative to a transducer with a single ultrasonic source. However, since the notch is provided on the ring surface opposite to the ultrasonic source of the ultrasonic transducer, the effective emitting area of the ultrasonic source on the ring surface is reduced, the notch may cause dispersion of the ultrasonic energy, and the energy of the focusing area of such ultrasound therapeutic applicator serving as an annular integral body is reduced, which is disadvantageous for the enhancement of focusing ability of the ultrasonic transducer. Meanwhile, the technical solution just enlarges the emitting area of the ultrasonic transducer to have a superposition of energy at the focus. When the frequency is relatively low, since the wavelength is relatively long, the focusing ability of the ultrasonic waves is poor and the focusing area is relatively large, thus the ultrasonic intensity of the focusing area is so weak that coagulation necrosis of an target area cannot be formed rapidly and effectively during the ultrasonic therapy. In the ultrasonic therapy of deep tissues of a human body or the like, ultrasonic waves need to pass through human skin, bone tissues, air containing tissues, nerve tissues and the like before reaching a focusing position. If a relatively high frequency is adopted for work, the ultrasound has poor penetrability in tissues, and the above tissues have functions such as absorbing the transmitted ultrasonic waves, which causes reduction and dispersion of energy in the focusing area; and the temperature of tissues will rise after the tissues absorb the ultrasonic waves. When the emitting power of the ultrasonic transducer is very large, the temperature rise of the tissues may cause accidental injuries thereof. Additionally, human tissues have a very big nonlinear effect on the ultrasonic waves, so, if the ultrasonic waves with high intensity are transmitted in human tissues, a large part of the ultrasonic waves will be transformed into higher harmonics of the ultrasonic waves and absorbed by the tissues. At that time, if the ultrasonic emitting power of the ultrasonic transducer is continuously increased, a bigger nonlinear effect will be produced, owing to which the increased ultrasonic energy cannot be effectively transmitted to the expected focusing area, and an acoustic saturation phenomenon occurs, thereby affecting the focusing of the ultrasonic waves.

It can be seen that the above technical problem cannot be effectively solved in the prior art by simply enlarging the emitting area of an ultrasonic transducer and performing superposition of energy.

Actually, the emission and reflection on the opposite surface of the ultrasonic source can be used to enhance focusing gain. For instance, Chinese patent (Publication No.: CN 101140354A) applied for previously by the present applicant discloses a resonant ultrasonic transducer with a resonant cavity comprising an ultrasonic transducer and an ultrasonic reflecting unit which are opposite to each other. Since the ultrasonic reflecting unit is equivalent to an ultrasonic transducer, the resonant cavity is practically formed by two symmetrically disposed ultrasonic transducers. Through resonance of the ultrasonic waves in the resonant cavity, the length of the focusing area of the ultrasonic waves in the direction of the acoustic axis is shorter than that in the case of simply using a single ultrasonic transducer (if two ultrasonic waves with the same frequency come face to face, there will be interference in the area where they meet; when the interference appears, they have the same phase at the central point and have different phases at other points, therefore, the superposition of the two ultrasonic waves will cause distribution away from the center to be weak and the ultrasonic focusing area to shorten), so that the energy is more concentrated and the focusing gain is greatly enhanced. The work mode of the resonant ultrasonic transducer can bring a larger gain to the focusing area of the transducer without increasing the emitting area of the transducer.

Nevertheless, the ultrasonic transducer with such structure has many disadvantages: firstly, the resonant cavity formed by the two transducers is not a sealed annular sphere surface and cannot achieve effective acoustic resonance, and a part of energy may still escape from the opening portion between the two transducers provided opposite to each other, and therefore the ultrasonic energy emitted by the transducers cannot be used sufficiently; secondly, since the two transducers are provided opposite to each other, there is no fixed connection therebetween, which may easily result in the deviation of the two transducers from the resonance condition, so, it should be guaranteed that the ultrasonic path in which the two transducers emit the ultrasonic waves will not be interrupted by other factors, otherwise the desired resonant cavity between the two transducers provided opposite to each other may not be formed, and enough gain cannot be produced in the focusing area, or other focusing areas may be formed to damage other normal tissues; thirdly, the length of the focusing area is compressed only in the direction of the acoustic axis of the resonant cavity, and the lengths of the focusing areas in other directions deviated from the direction of the acoustic axis of the resonant cavity are not compressed, that is to say, the formed focusing area is compressed in its length only in the direction of the acoustic axis of the ultrasonic waves, and the volume of the focusing area is not reduced sufficiently; fourthly, the size of the focusing area of the ultrasonic transducer is still affected by frequency, and the ultrasound has poor tissue penetrability under a work condition of low frequency, so that the technical problem of a great loss of energy on the transmission path cannot be solved; fifthly, the emitting area of the ultrasonic transducer is not large enough.

SUMMARY OF THE INVENTION

The technical problem to be solved by the present invention is to, in view of the above deficiencies existing in the prior art, provide an ultrasonic transducer having a large ultrasonic emitting area, and focusing ability of ultrasonic waves that is hardly affected by the work frequency of an ultrasonic source.

The technical solution for solving the technical problem of the present invention is that the ultrasonic transducer includes one or a plurality of ultrasonic emitting units. The wavefronts of the ultrasonic waves emitted by the one or the plurality of ultrasonic emitting units are sphere surfaces with uniform radius, and the one or the plurality of ultrasonic emitting units have a function of reflecting ultrasound. The one ultrasonic emitting unit is configured to form a spherical resonant cavity, or the plurality of ultrasonic emitting units are configured to form a spherical resonant cavity collectively. An internal cavity of the spherical resonant cavity has a spherical shell shape or a cross-sectional spherical shell shape with a spherical center therein. The ultrasonic waves emitted by the one or the plurality of ultrasonic emitting units are focused on an area in which the spherical center of the spherical resonant cavity is located.

In the present invention, the internal cavity of the spherical resonant cavity formed by the ultrasonic emitting units has a spherical shell shape or a cross-sectional spherical shell shape with a spherical center therein, and the cavity surface of the whole spherical resonant cavity serves as an emitting surface and a reflecting surface of the ultrasonic waves, so that the effective ultrasonic emitting area is increased, and the number of times of reflection is increased. Meanwhile, after the spherical waves on the wavefront of each ultrasonic emitting unit are reflected back along the opposite direction of initial emitting paths, the reflected ultrasonic waves and the emitted ultrasonic waves, which have the same frequency, produce a resonance in the spherical resonant cavity. The two ultrasonic waves arrive at the spherical center at the same time, so that a plurality of resonance points are produced in the whole spherical resonant cavity. When the medium in the spherical resonant cavity absorbs few ultrasonic waves (a medium usually absorbs few ultrasonic waves when the ultrasonic waves have a relatively low frequency) and the ultrasonic emitting units have a favorable reflection of ultrasound, the ultrasonic waves emitted by the ultrasonic emitting units can be reflected for multiple times in the spherical resonant cavity, so that the ultrasonic waves can produce a plurality of times of resonance in the spherical resonant cavity. Since the spherical center of the spherical resonant cavity is also a resonance point, the ultrasonic waves emitted from the cavity surface of the spherical resonant cavity and the ultrasonic waves reflected by its opposite surface form a resonance-enhanced focusing area at the spherical center, thus enhancing the intensity of the ultrasonic waves at the spherical center and greatly improving the utilization rate of the ultrasonic waves. Moreover, when the ultrasonic energy emitted by the one or the plurality of ultrasonic emitting units and the energy of the reflected ultrasonic waves are centralized at the spherical center which undergoes a plurality of times of resonance enhancing, the energy increases several times, thereby enhancing the resonance at the spherical center and the energy of the focusing area. However, the resonance enhancing points, which are not positioned at the spherical center, undergo limited times of resonance, so that the ultrasonic energy of the positions in the spherical resonant cavity other than the spherical center is quite low compared with the ultrasonic energy at the spherical center. Thus, when a treated part is at the spherical center, the damage to other parts requiring no treatment can be effectively avoided.

If an existing conventional ultrasonic transducer is used to directly focus for treating a human body, suppose the sound pressure at the focus is P, and the sound intensity is I; also, the ultrasonic transducer of the present invention is used to treat a human body, suppose the frequency of the ultrasonic waves emitted by the ultrasonic emitting units is the same as the frequency when using the conventional ultrasonic transducer to perform treatment, and suppose the attenuation of the ultrasonic transducer in the present invention to ultrasound is about 10%. After first reflection, the sound pressure of the ultrasonic waves is attenuated to about 0.9 times the initial one, i.e. the sound pressure is attenuated to 0.9 P, and the sound pressure is attenuated to 0.81 times the initial one after two times of attenuation (suppose there are only two times of reflection, and the practical times of reflection is far more than two), i.e. the sound pressure is attenuated to 0.81 P. At that time, the sound pressure after superposition at the spherical center is P+0.9 P+0.81 P=2.71 P. Since the emission and reflection of the ultrasonic waves are both performed twice (the ultrasonic emitting units can emit and reflect ultrasound), the overall sound pressure at the spherical center is 2×2.71 P=–5.42 P. The sound intensity has a square relationship with the sound pressure, so the sound intensity at the spherical center in the focusing area turns into $5.42^2$ I=29.3764 I. Therefore, in the event that only two times of reflection of the ultrasonic waves are calculated, the energy of the ultrasonic transducer of the present invention reaches almost 30 times that of the conventional ultrasonic transducer. However, in practical application, with increase of the times of reflection and further reduction of attenuation amount, the focused energy will be larger. It can be seen that the ultrasonic energy at the focusing area of the ultrasonic transducer in the present invention is far larger than that of the existing ultrasonic transducer.

The spherical resonant cavity formed by the ultrasonic transducer in the present invention has a spherical shell shape or a cross-sectional spherical shell shape with a spherical center therein. When the internal cavity of the spherical resonant cavity has a spherical shell shape, it is a spherical resonant cavity with a completely closed sound path (or a sealed sound path), and the ultrasonic waves are only transmitted in the resonant cavity without being dispersed outside the resonant cavity. When the internal cavity of the spherical resonant cavity has a cross-sectional spherical shell shape with a spherical center therein, the expression "with a spherical center therein" means that the shape of the internal cavity formed by the spherical resonant cavity has a closed sound path in the circumferential direction which is perpendicular to the central axis and passes through the spherical center, that is, the curves forming the internal cavity include circumferential curves passing through the spherical center, which guarantees that the spherical resonant cavity forms a closed sound path (or a sealed sound path, i.e. a sound field distribution mode having no sound wave leakage in the circumferential direction, owing to which no diffraction appears in the circumferential direction and favorable focusing can be realized) in the circumferential direction which is perpendicular to the central axis. Thus, compared with previous ultrasonic transducers (e.g. Chinese patent CN 101140354A), the ultrasonic transducer in the present invention can prevent all or most ultrasonic energy from escaping from the resonant cavity.

Since the ultrasonic energy focusing area of a focusing ultrasonic transducer is caused by edge diffraction of the vibration emitting surface of the ultrasonic transducer, a traditional focusing ultrasonic transducer may cause dispersion of the ultrasonic energy focusing area owing to the edge effect of the ultrasonic emitting surface, and with reduction of the work frequency of the ultrasonic transducer, the edge effect will have more influences, thereby weakening ultrasonic focusing ability (i.e. enlarging focusing area). Therefore, when performing ultrasonic therapy, in order to form coagulation necrosis at a treated part, a common ultrasonic transducer needs to be operated with relatively high work frequency usually ranging from 0.8 MHZ to 10 MHZ. However, in the spherical resonant cavity formed by the ultrasonic transducer in the present invention, since it has a closed sound path in one or more directions of ultrasonic propagation, no diffraction will be produced in the circumferential direction of the focusing area, and thus reduction of ultrasonic focusing ability caused by reduction of ultrasonic frequency will not appear. Therefore, the size of the focusing area in the present invention is hardly affected by the emitting frequency of the ultrasonic transducer (certainly, for an ultrasonic transducer whose internal cavity of the spherical resonant cavity has a cross-sectional spherical shell shape with a spherical center therein, it is only guaranteed that the ultrasonic focusing area is compressed in the circumference which passes through the spherical center and is perpendicular to the acoustic axis, i.e. the focusing area is only compressed in all directions of the sound propagating plane, so that certain edge diffraction exists along the direction of the central axis). Therefore, the lower limit range value of the work frequency of the ultrasonic emitting units in the present invention can be appropriately small relative to that of the ultrasonic emitting units in the existing ultrasonic transducer, the range of the work frequency of the ultrasonic emitting units is from 20 kHz to 10 MHz, and the preferable range of the work frequency is from 0.1 MHz to 0.8 MHz.

The focusing ability of the ultrasonic transducer in the present invention is far better than that of a traditional ultrasonic transducer, therefore, even if it works at a low frequency such as 20 kHz, the ultrasonic transducer of the present invention can work effectively to realize effective treatment to a human body, whereas the traditional ultrasonic transducer cannot produce a high sound field at such low frequency. With low work frequency and temperature rise of tissue, the ultrasonic transducer of the present invention can perform safe and effective treatment to some tissue organs that contain air containing tissues and bone tissues or are sheltered by other tissues of human body. Additionally, the number of times of ultrasonic reflection in actual treatment is limited, and the ultrasonic emitting units in the ultrasonic transducer in the present invention also serve as ultrasonic reflecting units (the ultrasonic emitting units can reflect ultrasound) and have strong focusing ability, so that the ultrasonic emitting units can work under the condition of low frequency. Reduction of the work frequency of the ultrasonic emitting units favors increase of the number of times of ultrasonic reflection (the lower the frequency is, the less ultrasound tissues absorb, the more the reflection occurs), so that the ultrasonic intensity at the focusing area (the spherical center) can be further increased.

When designing the spherical resonant cavity of the present invention, it is required to guarantee that the spherical resonant cavity formed by the ultrasonic emitting units which emit spherical waves satisfies ultrasonic resonance superposition principle, that is, the diameter of the spherical resonant cavity is an integral multiple of the half wavelength of the emitted ultrasonic waves.

In the present invention, when the internal cavity of the spherical resonant cavity has a cross-sectional spherical shell shape with a spherical center therein, the internal cavity having the cross-sectional spherical shell shape with the spherical center therein can be a truncated cross-sectional spherical shell-shape internal cavity (the height of the cavity is larger than the spherical radius) or a frustum shaped cross-sectional spherical shell-shape internal cavity.

When the internal cavity of the spherical resonant cavity is a frustum shaped cross-sectional spherical shell-shape internal cavity with a spherical center therein, the following forms can be used:

One is that an upper bottom surface S1 and a lower bottom surface S2 of the above internal cavity are parallel to each other, and the distance between the upper bottom surface and the spherical center is not equal to the distance between the lower bottom surface and the spherical center.

The other is that an upper bottom surface S1 and a lower bottom surface S2 of the above internal cavity are parallel to each other, and the distance between the upper bottom surface and the spherical center is equal to the distance between the lower bottom surface and the spherical center, which can keep the focusing gain at the spherical center as large as possible.

Certainly, in practical application, if the above two forms of spherical resonant cavity with frustum shaped cross-sectional spherical shell-shape internal cavity cannot be used for treatment (e.g. in the case of treating diseases such as hysteromyoma), the internal cavity of the spherical resonant cavity may be in an irregular frustum-shaped cross-sectional spherical shell shape. In such case, the upper bottom surface of the internal cavity is not parallel to the lower bottom surface thereof, and the distance between the upper bottom surface and the spherical center is equal to or is not equal to the distance between the lower bottom surface and the spherical center.

When the internal cavity of the spherical resonant cavity is a truncated cross-sectional spherical shell-shape internal cavity, it comprises a crown shaped spherical cavity, and a frustum shaped spherical cavity with a spherical center therein. The bottom surface of the crown shaped spherical cavity is fitted with and connected to one bottom surface of the frustum shaped spherical cavity. The connection between the crown shaped spherical cavity and the frustum shaped spherical cavity is removable or fixed.

The internal cavity of the spherical resonant cavity may have a complete spherical shell shape.

In the present invention, one ultrasonic emitting unit is one wave source, the spherical resonant cavity formed by one or more ultrasonic emitting units may have a housing of any shape, and it is only required to guarantee that the internal cavity of the spherical resonant cavity has a spherical shell shape or a cross-sectional spherical shell shape with a spherical center therein. When the internal cavity of a manufactured spherical resonant cavity has a complete spherical shell shape, the spherical resonant cavity can be formed only by one ultrasonic emitting unit having a spherical shell shape; or the cavity having a spherical shell shape can be divided into a plurality of small pieces each of which is an ultrasonic emitting unit, and all ultrasonic emitting units can emit spherical waves having equal radius. That is to say, the spherical resonant cavity having a spherical shell shape can be formed by a plurality of ultrasonic emitting units which emit spherical waves having equal radius. The ultrasonic emitting units can be manufactured from piezoelectric materials of any type as long as the condition that the ultrasonic waves emitted from the wavefronts of the ultrasonic emitting units are spherical waves is satisfied. For instance, a combination of piezoelectric materials capable of emitting planar ultrasonic waves and focusing lenses, which forms a lens focusing ultrasonic transducer unit, can be used, and a plurality of the lens focusing ultrasonic transducer units can be used to form an internal cavity having a spherical shell shape together. Wherein, the focusing lenses have an equal distance to the spherical center, and the internal cavity of the spherical resonant cavity formed by joining the inner surfaces of all focusing lenses together has a spherical shell shape or a cross-sectional spherical shell shape with a spherical center therein. Since an ultrasonic emitting unit of such type can also emit spherical waves, it meets the condition of ultrasonic emitting units in the present invention.

When designing the spherical resonant cavity, the ultrasonic emitting units should satisfy ultrasonic resonance superposition principle, that is, the diameter of the formed spherical resonant cavity is an integral multiple of the half wavelength of the ultrasonic waves.

When the internal cavity of the above spherical resonant cavity has a complete spherical shell shape, although the ultrasonic energy at the spherical center can be enhanced to the greatest extent, an ultrasonic transducer with such spherical resonant cavity can effectively treat a nidus in practical application only if the ultrasonic transducer has very large volume (for instance, it can accommodate the whole body of a person). Thus, based on the requirements of treatment, for instance, when treating a human head, preferably, the internal cavity of the spherical resonant cavity having a spherical shell shape comprises a truncated spherical cavity (the height of the cavity is larger than the spherical radius) and a crown shaped spherical cavity (the height of the cavity is smaller than the spherical radius). The bottom surface of the truncated spherical cavity is fitted with and connected to the bottom surface of the crown shaped spherical cavity. The connection between the truncated spherical cavity and the crown shaped spherical cavity is removable or fixed. When the connection between the truncated spherical cavity and the crown shaped spherical cavity is removable, only the truncated spherical cavity may be used in the case of treating a human head, and the ultrasonic waves emitted and reflected by the ultrasonic emitting units form a resonance-enhanced focusing area at the spherical center.

When the internal cavity of the spherical resonant cavity formed by the ultrasonic transducer is a truncated spherical resonant cavity, the focusing area of such ultrasonic transducer is compressed only in a direction perpendicular to the direction of the acoustic axis (i.e. the central axis of the spherical resonant cavity), but not in the direction of the acoustic axis. Therefore, the focusing gain of the ultrasonic transducer at the spherical center is weaker than that of an ultrasonic transducer with an internal cavity having a spherical shell shape.

Or the spherical shell shaped internal cavity of the spherical resonant cavity comprises a frustum shaped spherical cavity with a spherical center therein and two crown shaped spherical cavities respectively provided at the upper and lower ends of the frustum shaped spherical cavity.

The spherical shell shaped internal cavity of the spherical resonant cavity can also comprise a frustum shaped spherical cavity with a spherical center therein and two crown shaped spherical cavities respectively provided at the upper and lower ends of the frustum shaped spherical cavity. The bottom surfaces of the two crown shaped spherical cavities are fitted with and connected to the upper bottom surface and lower bottom surface of the frustum shaped spherical cavity respectively. The connection between the frustum shaped spherical cavity and each crown shaped spherical cavity is removable or fixed. When the connection between the frustum shaped spherical cavity and each crown shaped spherical cavity is removable, only the frustum shaped spherical cavity may be used in the case of treating a human torso and limbs, and the ultrasonic waves emitted and reflected by the ultrasonic emitting units form a resonance-enhanced focusing area at the spherical center.

Preferably, the two bottom surfaces of the above frustum shaped spherical resonant cavity are parallel to each other and have an equal or different distance to the spherical center, and the specific distance can be designed based on requirements in practical application. In order to keep the focusing gain at the spherical center as large as possible, preferably, the two bottom surfaces of the frustum shaped spherical cavity have an equal distance to the spherical center.

When the internal cavity of the spherical resonant cavity formed by the ultrasonic transducer is a frustum shaped spherical resonant cavity, since the ultrasound focusing area is only compressed within the circumference, that is, it is only compressed in all directions of the sound propagation plane, certain edge diffraction still exists along the direction of the central axis of the ultrasonic transducer. Thus, the focusing gain at the spherical center of the ultrasonic transducer is weaker than that of an ultrasonic transducer whose spherical resonant cavity has a truncated spherical internal cavity.

Preferably, a hole to be passed through by an image monitoring device is opened on the above formed spherical resonant cavity.

The ultrasonic transducer in the present invention comprises one or a plurality of ultrasonic emitting units. In the case of one ultrasonic emitting unit, the ultrasonic emitting unit forms a complete spherical shell shaped spherical resonant cavity.

A plurality of ultrasonic emitting units can be used in the present invention, and different ultrasonic emitting units can emit ultrasonic waves having different frequencies. When the frequencies of the ultrasonic waves emitted by the ultrasonic emitting units are different from one another, although all ultrasonic emitting units having different frequencies can form energy superposition at the focus, such energy superposition is not coherent superposition. Thus, high energy like that produced under coherent superposition cannot be obtained at the focus (the spherical center), but energy superposition can be formed at the focus, because the emitted energy of such manner of superposition is far larger than that in the case of using a single wave source. In order to improve the ultrasonic energy at the focusing area and form stable ultrasonic resonance, preferably, the difference among the frequencies of the spherical waves emitted by the ultrasonic emitting units is within 20%. Further preferably, the spherical waves emitted by the ultrasonic emitting units have the same frequency to form resonance, thereby forming coherent superposition of the ultrasonic energy at the spherical center and further increasing the ultrasonic energy.

When the ultrasonic transducer in the present invention has one ultrasonic emitting unit or a plurality of ultrasonic emitting units having the same frequency, a spherical resonant cavity is formed. All ultrasonic waves emitted and reflected in this spherical resonant cavity pass through the spherical center, and the ultrasonic energy at the spherical center is superposed in a way of in-phase superposition, so that the ultrasonic energy is greatly enhanced. For resonance points which are not at the spherical center in the spherical resonant cavity, since the superposition of the ultrasonic energy at said resonance points is not an in-phase superposition, the ultrasonic energy at said resonance points is weakened. Thus, when using the ultrasonic transducer in the present invention to treat a human body, it can be guaranteed to the greatest extent that nidus tissues at the focus receive great ultrasonic energy and other human tissues which are not at the focus are safe.

The diffraction mechanism of the ultrasonic transducer in the present invention is similar to the diffraction mechanism in optics. When the ultrasonic transducer in the present invention has a spherical resonant cavity having a cross-sectional spherical shell shape with a spherical center therein, since the open-type ultrasonic transducer still has diffraction phenomena in the circumferential direction which is perpendicular to the acoustic axis, the length of the focusing area in the direction is not compressed; when the ultrasonic transducer in the present invention has a spherical resonant cavity having a spherical shell shape, the whole sound path is completely closed and no diffraction occurs, so that the energy at the focus is the largest.

The ultrasonic transducer in the present invention well solves the problems in the ultrasonic treatment to deep tissue diseases of a human body and intracranial ultrasonic treatment. Under the condition that the safety of a human body is guaranteed, enough ultrasonic energy can reach deep tissues of a human body, and thermal damage caused by the absorption of ultrasonic waves by bone tissues on the ultrasonic path is avoided. Therefore, the ultrasonic transducer in the present invention is particularly suitable for treating deep tissues of a human body and intracranial nidus.

The ultrasonic transducer in the present invention not only can be provided with large ultrasonic emitting area and great focusing gain that render the energy of the ultrasonic focus enhanced dramatically, but also can be free from the influence of the work frequency of the ultrasonic source.

Compared with an existing ultrasonic transducer, the ultrasonic transducer in the present invention has the following advantages: (1) the size of the focusing area of the ultrasonic waves emitted by the ultrasonic transducer in the present invention is hardly affected by the frequency of the ultrasonic emitting unit, and coagulation necrosis can be well formed in a nidus by using low-frequency ultrasonic waves; (2) the lengths along all directions of the focusing area of ultrasonic waves can be effectively compressed to greatly reduce the volume of the focusing area, thereby enhancing the ultrasonic intensity at the focusing area; and (3) the ultrasonic intensity at the focusing area is enhanced by means of resonance of the ultrasonic waves with no need to increase the emitting power of the ultrasonic waves, thereby avoiding the enhancement of ultrasonic intensity at the non-focusing area and guaranteeing the safety of the parts which are not to be treated.

Figure 1:
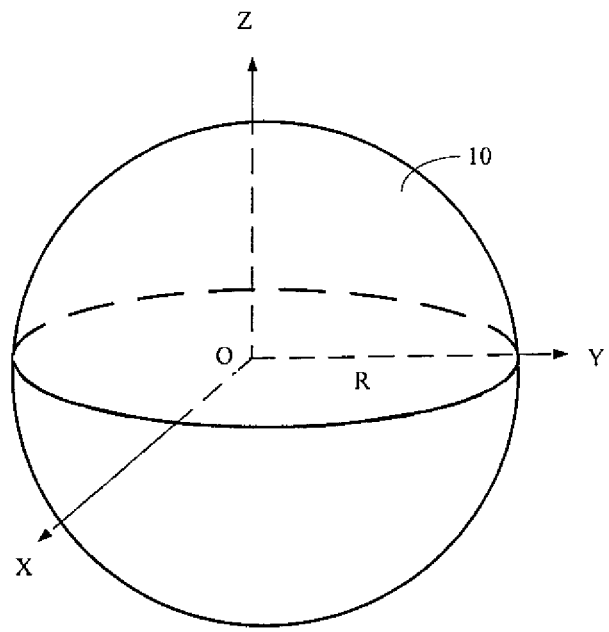
FIG. 1 is a structural schematic diagram of a shell shaped spherical resonant cavity in Embodiment 1 of the present invention.

In the drawings, the following reference numerals and signs are used:

1—ultrasonic emitting unit, 10—shell shaped spherical cavity, 11—crown shaped spherical cavity, 12—truncated spherical cavity, 13,14—frustum shaped spherical cavity, 15—planar piezoelectric wafer, 16—focusing lens, 20—hole, h1—height of crown shaped spherical cavity, h2—height of truncated spherical cavity, R—spherical radius, S1—upper bottom surface, S2—lower bottom surface

DETAILED DESCRIPTION OF THE PREFERRED EMBODIMENTS

The present invention will be further described in detail in connection with the drawings and the embodiments hereinafter.

The ultrasonic transducer in the present invention includes one or a plurality of ultrasonic emitting units. The wavefronts of the ultrasonic waves emitted by the one or the plurality of ultrasonic emitting units are sphere surfaces with uniform radius, and the one or the plurality of ultrasonic emitting units have a function of reflecting ultrasound. The one ultrasonic emitting unit is configured to form a spherical resonant cavity, or the plurality of ultrasonic emitting units are configured to form a spherical resonant cavity collectively. The internal cavity of the spherical resonant cavity has a spherical shell shape or a cross-sectional spherical shell shape with a spherical center therein. The ultrasonic waves emitted by the one or the plurality of ultrasonic emitting units are focused on an area in which the spherical center of the spherical resonant cavity is located.

The following embodiments are nonrestrictive embodiments of the present invention.

Embodiment 1

In this embodiment, the ultrasonic transducer comprises one ultrasonic emitting unit which has a function of reflecting ultrasound, and the ultrasonic emitting unit is a self-focusing ultrasonic transducer unit. The wavefront of the ultrasonic waves emitted by the ultrasonic emitting unit is a sphere surface with uniform radius, and the emitted ultrasonic waves are spherical waves. The ultrasonic emitting unit is configured to form a spherical resonant cavity, the internal cavity of which has a complete spherical shell shape so as to form a shell shaped spherical resonant cavity with a completely closed sound path. The focusing area of the shell shaped spherical resonant cavity is an area in which the spherical center of the spherical resonant cavity is located.

In the ultrasonic transducer of the present invention, the ultrasonic waves emitted by the ultrasonic emitting unit and the ultrasonic waves emitted or reflected by its opposite surface form a resonance-enhanced focusing area at the spherical center.

Wherein, the ultrasonic emitting unit can be manufactured from self-focusing ultrasonic piezoelectric materials having various shapes. For convenient manufacture, the ultrasonic transducer in the present invention can be directly manufactured in the form of a shell shaped spherical cavity 10 shown in FIG. 1. Certainly, a housing of any shape can be added outside the manufactured spherical resonant cavity, that is, it only requires that the internal cavity of the spherical resonant cavity has a complete spherical shell shape.

The shell shaped spherical cavity 10 in this embodiment is of an openable type for placing objects inside, and the specific position of its openable part can be set based on the objects that need to be placed in the shell shaped spherical cavity 10.

The ultrasonic transducer in this embodiment is mainly suitable for some medical experiments capable of being performed in a sealed environment. For instance, stereo organs or phantoms for experiments or other objects are first placed inside the shell shaped spherical cavity 10 of the ultrasonic transducer, and then the whole shell shaped spherical cavity 10 is sealed to start treatments or experiments. After the treatments or experiments, the shell shaped spherical cavity 10 is opened to check the effect of the treatments or experiments. The situation of the treatments or experiments is taken as a guide for clinical use.

When the volume of the shell shaped spherical cavity 10 is very large, for instance, when it is large enough to accommodate a whole human body, the ultrasonic transducer can also be used for treating a human body.

Embodiment 2

Figure 2:
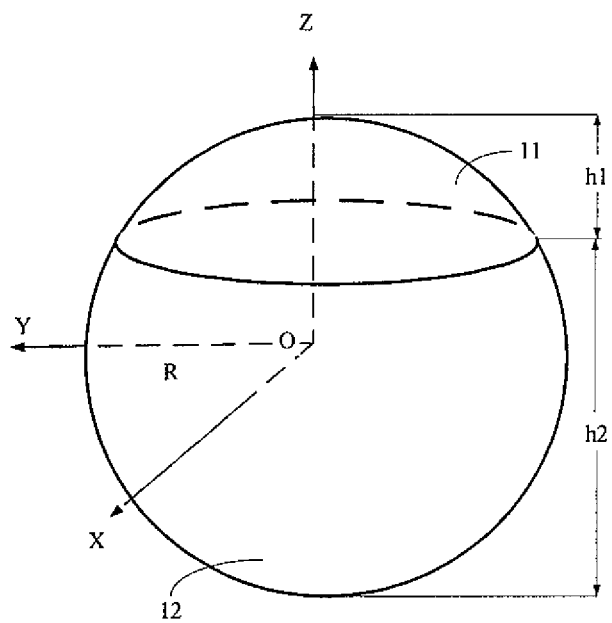
FIG. 2 is a structural schematic diagram of a shell shaped spherical resonant cavity in Embodiment 2 of the present invention.
Figure 3:
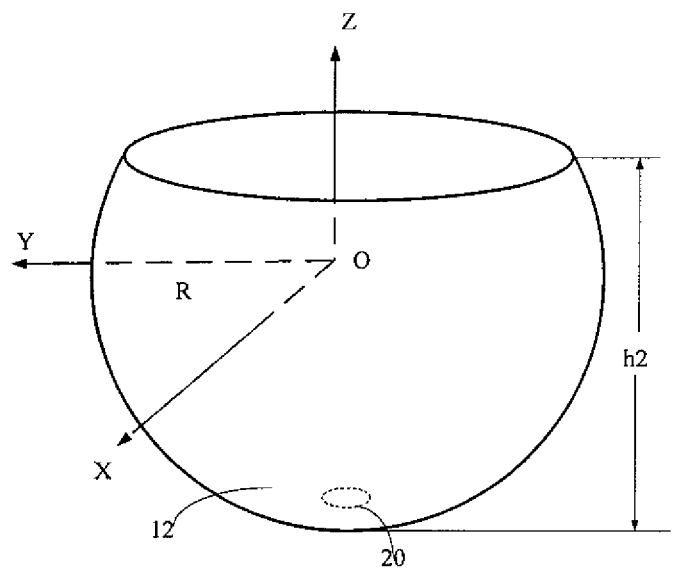
FIG. 3 is a structural schematic diagram of a truncated spherical resonant cavity in Embodiment 2 of the present invention (one ultrasonic emitting unit is used)
Figure 4:
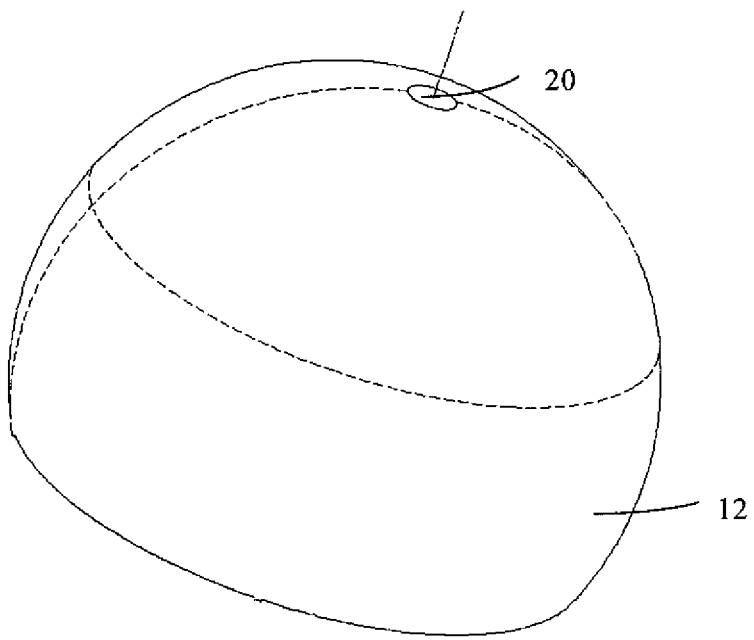
FIG. 4 is a structural schematic diagram of the truncated spherical resonant cavity in Embodiment 2 of the present invention (a plurality of ultrasonic emitting units are used)

As shown in FIG. 2, in this embodiment, the internal cavity of the spherical resonant cavity formed by the ultrasonic transducer has a complete spherical shell shape, and the difference between Embodiment 2 and Embodiment 1 lies in that the spherical resonant cavity having a spherical shell shape is not formed by only one ultrasonic emitting unit. The internal cavity of the spherical resonant cavity having a spherical shell shape is formed by a truncated spherical cavity 12 (as shown in FIGS. 3 and 4) and a crown shaped spherical cavity 11 together. The bottom surface of the truncated spherical cavity 12 is fitted with and connected to the bottom surface of the crown shaped spherical cavity 11, and the connection between the truncated spherical cavity 12 and the crown shaped spherical cavity 11 is removable.

Wherein, the height h1 of the crown shaped spherical cavity 11 is smaller than the spherical radius R, and the height h2 of the truncated spherical cavity 12 is larger than the spherical radius R.

In order to conveniently position a target area, monitor treatment process and perform efficacy evaluation in time, in this embodiment, as shown in FIGS. 3 and 4, a hole 20 to be passed through by an image monitoring device is opened in the truncated spherical cavity 12, or the hole 20 can be opened in the crown shaped spherical cavity 11.

In this embodiment, the truncated spherical cavity 12 can be formed by one ultrasonic emitting unit 1 (as shown in FIG. 3), and in order to simplify the manufacturing process, it can be formed by joining a plurality of ultrasonic emitting units together (as shown in FIG. 4). For the same reason, the crown shaped spherical cavity 11 can be formed by one ultrasonic emitting unit 1, and it can also be formed by joining a plurality of ultrasonic emitting units together. The one or the plurality of ultrasonic emitting units are configured as self-focusing ultrasonic transducer units which can reflect ultrasonic waves. The wavefronts of the ultrasonic waves emitted by the one or the plurality of ultrasonic emitting units are sphere surfaces with uniform radius.

In the above truncated spherical cavity 12 which has a plurality of ultrasonic emitting units, the difference among frequencies of the ultrasonic waves emitted by the plurality of ultrasonic emitting units is within 20%, and preferably, the ultrasonic waves emitted by the plurality of ultrasonic emitting units have the same frequency.

In this embodiment, the truncated spherical cavity 12 is suitable for treating a human head. Only the truncated spherical cavity 12 is used when treating a human head. A human head is first made to enter the truncated spherical cavity 12; since the ultrasonic waves emitted and reflected by the ultrasonic emitting units form a resonance-enhanced focusing area at the spherical center, the human nidus is placed at the spherical center; and then the ultrasonic emitting units which form the truncated spherical cavity 12 are started for performing treatment.

As a matter of fact, the above truncated spherical cavity 12 can form an ultrasonic transducer whose internal cavity is a truncated spherical resonant cavity by itself. In the ultrasonic transducer, a housing of any shape can be added outside its cavity based on requirements (or no housing is added).

Embodiment 3

Figure 5:
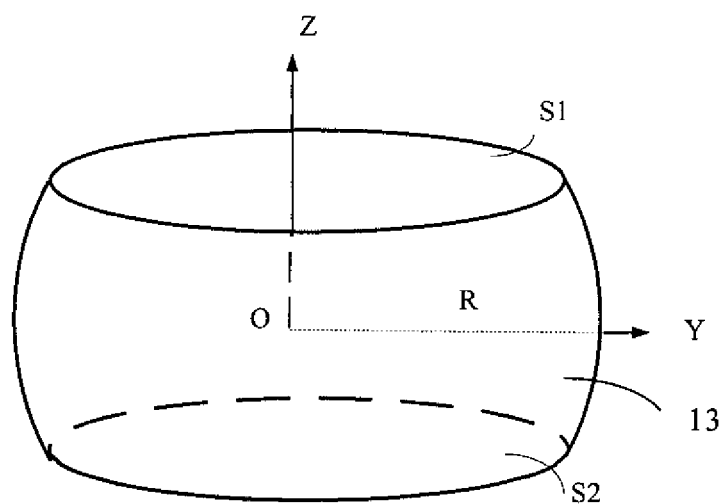
FIG. 5 is a structural schematic diagram of a (regular) frustum shaped spherical resonant cavity in Embodiment 3 of the present invention (one ultrasonic emitting unit is used)
Figure 6:
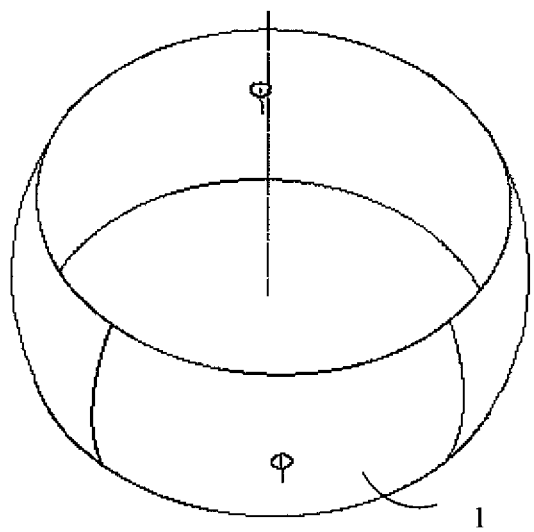
FIG. 6 is a structural schematic diagram of a (regular) frustum shaped spherical resonant cavity (having two bottom surfaces parallel to each other) in Embodiment 3 of the present invention (a plurality of ultrasonic emitting units arranged in a single layer are used)
Figure 7:
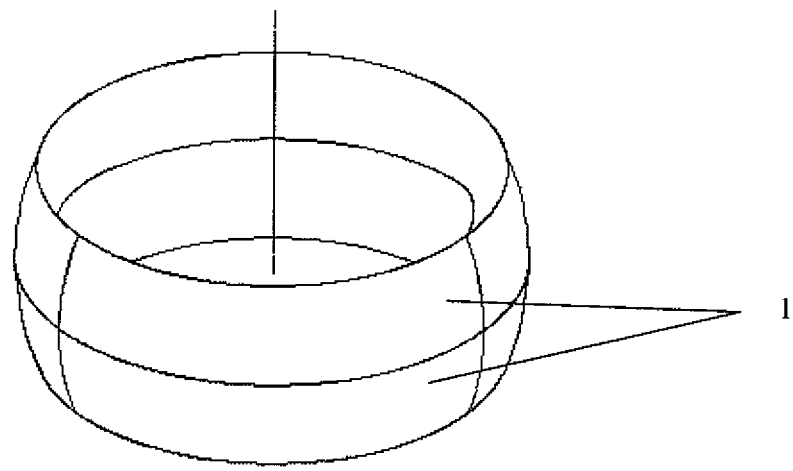
FIG. 7 is a structural schematic diagram of a (regular) frustum shaped spherical resonant cavity (having two bottom surfaces parallel to each other) in Embodiment 3 of the present invention (a plurality of ultrasonic emitting units arranged in multiple layers are used)

As shown in FIGS. 5, 6 and 7, in this embodiment, the internal cavity of the spherical resonant cavity formed by the ultrasonic transducer has a cross-sectional spherical shell shape with a spherical center therein, and the internal cavity is configured as a regular frustum shaped spherical cavity 13.

In this embodiment, the upper bottom surface S1 and the lower bottom surface S2 of the frustum shaped spherical cavity 13 are parallel to each other, and the distance between the upper bottom surface S1 and the spherical center O is equal to the distance between the lower bottom surface S2 and the spherical center O.

In this embodiment, the frustum shaped spherical cavity 13 can be formed from one ultrasonic emitting unit 1 (as shown in FIG. 5), or a plurality of ultrasonic emitting units 1 arranged in a single layer (as shown in FIG. 6), or a plurality of ultrasonic emitting units 1 arranged in multiple layers (as shown in FIG. 7). The one or the plurality of ultrasonic emitting units are configured as self-focusing ultrasonic transducer units which can reflect ultrasonic waves. Wherein, the Z-axis direction shown in FIG. 5 is the acoustic axis direction of the frustum shaped spherical cavity 13, and the Z-axis coincides with the central axis of the frustum shaped spherical cavity 13.

When the frustum shaped spherical cavity 13 is formed by joining a plurality of ultrasonic emitting units together, the ultrasonic waves emitted by the plurality of ultrasonic emitting units have the same frequency. The wavefronts of the ultrasonic waves emitted by the ultrasonic emitting units are sphere surfaces with uniform radius.

The ultrasonic transducer in this embodiment is suitable for treating a human torso or limbs. When treating a human torso or limbs, the human torso or limbs are first made to pass through the frustum shaped spherical cavity 13, the nidus is placed at the spherical center, and then the ultrasonic emitting units are started for performing the treatment.

Embodiment 4

Figure 8:
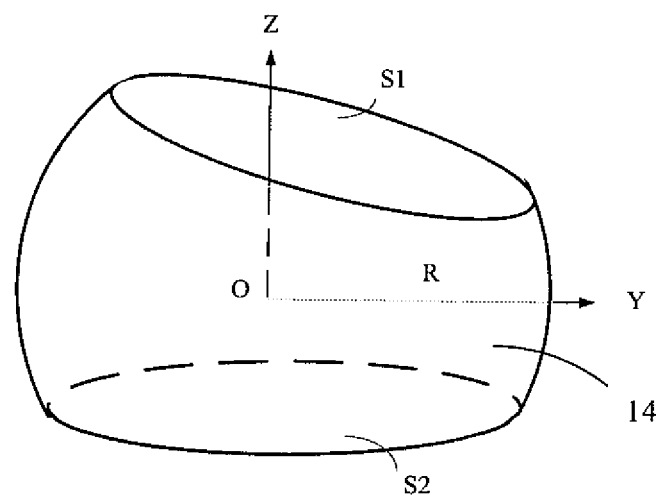
FIG. 8 is a structural schematic diagram of a (irregular) frustum shaped spherical resonant cavity (having two non-parallel bottom surfaces) in Embodiment 4 of the present invention.

As shown in FIG. 8, in this embodiment, the internal cavity of the spherical resonant cavity formed by the ultrasonic transducer has a cross-sectional spherical shell shape with a spherical center therein, and the internal cavity is configured as an irregular frustum shaped spherical cavity 14.

In this embodiment, the upper bottom surface S1 and the lower bottom surface S2 of the frustum shaped spherical cavity 14 are not parallel to each other. And the distance between the upper bottom surface S1 and the spherical center O is equal to the distance between the lower bottom surface S2 and the spherical center O.

In this embodiment, the frustum shaped spherical cavity 14 can be formed by one ultrasonic emitting unit 1, or a plurality of ultrasonic emitting units 1 arranged in a single layer, or a plurality of ultrasonic emitting units 1 arranged in multiple layers. The one or the plurality of ultrasonic emitting units are configured as self-focusing ultrasonic transducer units which can reflect ultrasonic waves. Wherein, the Z-axis direction shown in FIG. 8 is the acoustic axis direction of the frustum shaped spherical cavity 14, and the Z-axis coincides with the central axis of the frustum shaped spherical cavity 14.

When the frustum shaped spherical cavity 14 is formed by joining a plurality of ultrasonic emitting units together, the ultrasonic waves emitted by the plurality of ultrasonic emitting units have the same frequency. The wavefronts of the ultrasonic waves emitted by the ultrasonic emitting units are sphere surfaces with uniform radius.

The ultrasonic transducer in this embodiment is suitable for treating hysteromyoma and other diseases. When treating hysteromyoma and other diseases, in order to be adapted for a special postural therapy, the ultrasonic transducer having the irregular frustum shaped spherical resonant cavity in this embodiment can be used.

Embodiment 5

Figure 9:
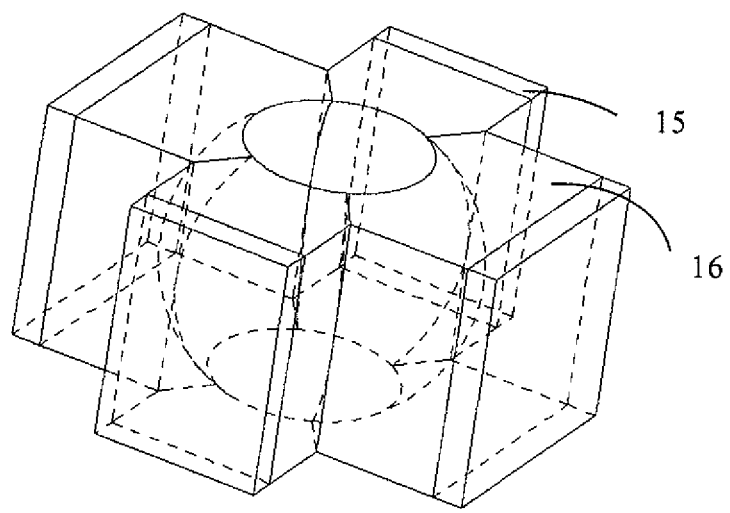
FIG. 9 is a structural schematic diagram of an ultrasonic transducer in Embodiment 5 of the present invention.
Figure 10:
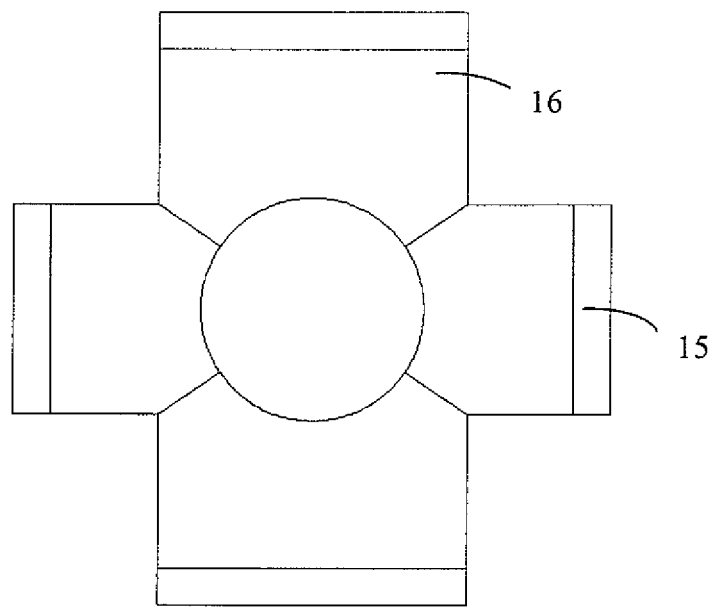
FIG. 10 is a top view of the ultrasonic transducer in FIG. 9.
Figure 11:
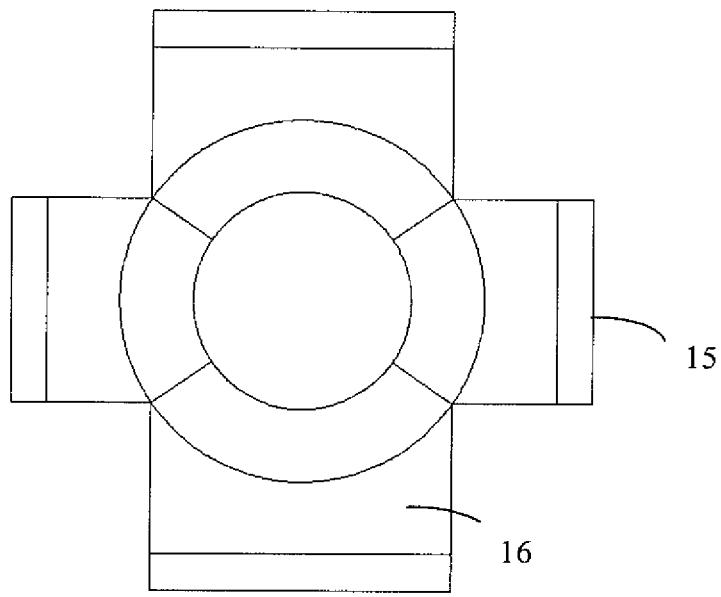
FIG. 11 is a semi-sectional view of the ultrasonic transducer in FIG. 9.

The difference between this embodiment and Embodiment 3 lies in that the ultrasonic emitting unit in the ultrasonic transducer of this embodiment is formed by a combination of piezoelectric materials capable of emitting planar ultrasonic waves and focusing lenses, that is, the ultrasonic emitting unit is configured as a lens focusing ultrasonic transducer unit. As shown in FIGS. 9, 10 and 11, in this embodiment, the spherical resonant cavity is formed by four planar piezoelectric wafers 15 and four focusing lenses 16, that is, each planar piezoelectric wafer 15 has one focusing lens 16 attached thereon. The ultrasonic waves emitted by the four lens focusing ultrasonic transducer units are also spherical waves, and the wavefronts of the emitted ultrasonic waves are sphere surfaces with uniform radius.

Since the inner surface of each of the above four focusing lenses 16 is one part of a sphere surface, all focusing lenses have an equal distance to the spherical center, and a frustum shaped spherical cavity with a spherical center therein can be formed by joining them together (certainly, a shell shaped spherical cavity or a truncated spherical cavity can also be formed by joining them together). That is to say, the internal cavity of the spherical resonant cavity formed by the ultrasonic transducer has a cross-sectional spherical shell shape with a spherical center therein, and the internal cavity of the spherical resonant cavity having a cross-sectional spherical shell shape is configured as a frustum shaped spherical cavity.

Other structures and applications thereof in this embodiment are the same as those in Embodiment 3 and will not be explained here.

It should be understood that the above embodiments are exemplary implementations simply for explaining the principle of the present invention, but the present invention is not limited to the above. A person skilled in the art can make various variations and improvements without departing from the spirit and substance of the present invention, and these variations and improvements are deemed as the scope of protection of the present invention.

The invention claimed is:

1. An ultrasonic transducer including one or a plurality of ultrasonic emitting units, wherein wavefronts of ultrasonic waves emitted by the one or the plurality of ultrasonic emitting units are sphere surfaces with uniform radius, the one or the plurality of ultrasonic emitting units have a function of reflecting ultrasound, the one ultrasonic emitting unit forms a spherical resonant cavity or the plurality of ultrasonic emitting units form a spherical resonant cavity collectively, an internal cavity of said spherical resonant cavity has a complete spherical shell shape or a cross-sectional spherical shell shape with a spherical center therein, and the ultrasonic waves emitted by the one or the plurality of ultrasonic emitting units are focused on an area in which the spherical center of said spherical resonant cavity is located.

2. The ultrasonic transducer according to claim 1, wherein the internal cavity of the spherical resonant cavity has the cross-sectional spherical shell shape with the spherical center therein, and said internal cavity having the cross-sectional spherical shell shape is configured as a truncated cross-sectional spherical shell-shape internal cavity or a frustum shaped cross-sectional spherical shell-shape internal cavity.

3. The ultrasonic transducer according to claim 2, wherein the internal cavity of said spherical resonant cavity is the frustum shaped cross-sectional spherical shell-shape internal cavity with the spherical center therein, an upper bottom surface (S1) and a lower bottom surface (S2) of said frustum shaped cross-sectional spherical shell-shape internal cavity are parallel to each other, and the distance between the upper bottom surface and the spherical center is equal to the distance between the lower bottom surface and the spherical center; or the internal cavity of said spherical resonant cavity is the frustum shaped cross-sectional spherical shell-shape internal cavity with the spherical center therein, an upper bottom surface (S1) and a lower bottom surface (S2) of said frustum shaped cross-sectional spherical shell-shape internal cavity are parallel to each other, and the distance between the upper bottom surface and the spherical center is not equal to the distance between the lower bottom surface and the spherical center.

4. The ultrasonic transducer according to claim 3, wherein the plurality of ultrasonic emitting units are used, and the ultrasonic waves emitted by the plurality of ultrasonic emitting units have the same frequency.

5. The ultrasonic transducer according to claim 2, wherein the internal cavity of said spherical resonant cavity is the frustum shaped cross-sectional spherical shell-shape internal cavity with the spherical center therein, an upper bottom surface (S1) and a lower bottom surface (S2) of said frustum shaped cross-sectional spherical shell-shape internal cavity are not parallel to each other, and the distance between the upper bottom surface and the spherical center is equal to or is not equal to the distance between the lower bottom surface and the spherical center.

6. The ultrasonic transducer according to claim 5, wherein the plurality of ultrasonic emitting units are used, and the ultrasonic waves emitted by the plurality of ultrasonic emitting units have the same frequency.

7. The ultrasonic transducer according to claim 2, wherein the truncated cross-sectional spherical shell-shape internal cavity comprises a crown shaped spherical cavity and a frustum shaped spherical cavity with the spherical center therein, a bottom surface of said crown shaped spherical cavity is fitted with and connected to one of the bottom surfaces of said frustum shaped spherical cavity, and the connection between said crown shaped spherical cavity and said frustum shaped spherical cavity is removable or fixed.

8. The ultrasonic transducer according to claim 7, wherein the plurality of ultrasonic emitting units are used, and the ultrasonic waves emitted by the plurality of ultrasonic emitting units have the same frequency.

9. The ultrasonic transducer according to claim 2, wherein the plurality of ultrasonic emitting units are used, and the ultrasonic waves emitted by the plurality of ultrasonic emitting units have the same frequency.

10. The ultrasonic transducer according to claim 1, wherein the internal cavity of the spherical resonant cavity has the spherical shell shape, said internal cavity having the spherical shell shape comprises a truncated spherical cavity and a crown shaped spherical cavity, a bottom surface of said truncated spherical cavity is fitted with and connected to a bottom surface of said crown shaped spherical cavity, and a connection between said truncated spherical cavity and said crown shaped spherical cavity is removable or fixed; or said internal cavity having the spherical shell shape comprises a frustum shaped spherical cavity with a spherical center therein, and two crown shaped spherical cavities respectively provided at upper and lower ends of said frustum shaped spherical cavity, bottom surfaces of said two crown shaped spherical cavities are fitted with and connected to an upper bottom surface and a lower bottom surface of the frustum shaped spherical cavity respectively, and a connection between said frustum shaped spherical cavity and the two crown shaped spherical cavities is removable or fixed.

11. The ultrasonic transducer according to claim 10, wherein the plurality of ultrasonic emitting units are used, and the ultrasonic waves emitted by the plurality of ultrasonic emitting units have the same frequency.

12. The ultrasonic transducer according to claim 1, wherein the plurality of ultrasonic emitting units are used, and ultrasonic waves emitted by the plurality of ultrasonic emitting units have the same frequency.

13. The ultrasonic transducer according to claim 12, wherein the range of the work frequency of the plurality of ultrasonic emitting units is from 20 kHz to 10 MHz.

14. The ultrasonic transducer according to claim 13, wherein the range of the work frequency of the plurality of ultrasonic emitting units is from 0.1 MHz to 0.6 MHz.

15. The ultrasonic transducer according to claim 12, wherein a hole (20) to be passed through by an image monitoring device is opened in said spherical resonant cavity.

16. The ultrasonic transducer according to claim 12, wherein the plurality of ultrasonic emitting units are configured as self-focusing ultrasonic transducer units or lens focusing ultrasonic transducer units.

17. The ultrasonic transducer according to claim 1, wherein the range of the work frequency of the one or the plurality of ultrasonic emitting units is from 20 kHz to 10 MHz.

18. The ultrasonic transducer according to claim 17, wherein the range of the work frequency of the one or the plurality of ultrasonic emitting units is from 0.1 MHz to 0.6 MHz.

19. The ultrasonic transducer according to claim 1, characterized in that a hole (20) to be passed through by an image monitoring device is opened in said spherical resonant cavity.

20. The ultrasonic transducer according to claim 1, wherein the one or the plurality of ultrasonic emitting units are configured as self-focusing ultrasonic transducer units or lens focusing ultrasonic transducer units.

* * * * *